(12) United States Patent
Thomsen

(10) Patent No.: US 11,352,195 B2
(45) Date of Patent: Jun. 7, 2022

(54) AEROSOL DISPENSERS AND CONTAINERS AND HEADS FOR SUCH CONTAINERS

(71) Applicant: DOC-BIBAWO APS, Kongens Lyngby (DK)

(72) Inventor: Martin Thomsen, København S (DK)

(73) Assignee: DOC BIBAWO A/S, Birkerød (DK)

( * ) Notice: Subject to any disclaimer, the term of this patent is extended or adjusted under 35 U.S.C. 154(b) by 112 days.

(21) Appl. No.: 16/470,178

(22) PCT Filed: Dec. 22, 2017

(86) PCT No.: PCT/EP2017/084401
§ 371 (c)(1),
(2) Date: Jun. 14, 2019

(87) PCT Pub. No.: WO2018/115447
PCT Pub. Date: Jun. 28, 2018

(65) Prior Publication Data
US 2019/0322442 A1 Oct. 24, 2019

(30) Foreign Application Priority Data

Dec. 23, 2016 (EP) .................... 16206663

(51) Int. Cl.
*B65D 83/20* (2006.01)
*B05B 12/20* (2018.01)
(Continued)

(52) U.S. Cl.
CPC ........ *B65D 83/206* (2013.01); *A61B 18/0218* (2013.01); *B05B 12/20* (2018.02);
(Continued)

(58) Field of Classification Search
CPC .. B65D 83/206; B65D 83/226; B65D 83/303; B65D 83/525; B65D 83/28; B65D 83/22; B65D 83/52; B65D 83/543; B65D 83/546
See application file for complete search history.

(56) References Cited

U.S. PATENT DOCUMENTS 2,375,215 A * 5/1945 Davis ................... B65D 83/207
222/394
3,189,232 A 6/1965 Joffe
(Continued)

FOREIGN PATENT DOCUMENTS

FR 2493515 A1 5/1982
JP H 11104022 A 4/1999
(Continued)

OTHER PUBLICATIONS

International Search Report and Written Opinion dated Apr. 23, 2018 for PCT Application No. PCT/EP2017/084401, 15 pages.

*Primary Examiner* — Frederick C Nicolas
*Assistant Examiner* — Randall A Gruby
(74) *Attorney, Agent, or Firm* — Squire Patton Boggs (US) LLP

(57) ABSTRACT

Heads for an aerosol container are disclosed. The head comprises a handle body having a base configured to be coupled to the aerosol container, an outlet, a flexible tube housed within the handle body. The flexible tube is configured to provide fluid communication between the container exit of the aerosol container and the outlet. And the head further comprises an elastically deformable actuator having a lever arm, and a coupling portion integrally formed with the lever arm and configured to be mounted around the flexible tube, wherein the coupling portion is further configured such that when the lever arm is deformed by a user, the coupling portion actuates on the valve body of the
(Continued)

aerosol container. Aerosol containers having such heads and kits for treatments skin lesions are also disclosed.

16 Claims, 6 Drawing Sheets

(51) Int. Cl.
    *A61B 18/02*     (2006.01)
    *B65D 83/22*     (2006.01)
    *B65D 83/30*     (2006.01)
    *B65D 83/52*     (2006.01)
    *B65D 83/14*     (2006.01)
    *A61B 18/00*     (2006.01)

(52) U.S. Cl.
    CPC ......... *B65D 83/226* (2013.01); *B65D 83/303* (2013.01); *B65D 83/525* (2013.01); *B65D 83/7532* (2013.01); *A61B 2018/0047* (2013.01)

(56) References Cited

U.S. PATENT DOCUMENTS

| | | | | |
|---|---|---|---|---|
| 3,580,432 A * | 5/1971 | Brooks | ................ | B65D 83/22 |
| | | | | 222/402.13 |
| 3,806,028 A | 4/1974 | Coffey | | |
| 4,871,092 A | 10/1989 | Maerte | | |
| 5,147,075 A * | 9/1992 | Regan | ................ | F17C 7/00 |
| | | | | 222/402.15 |
| 5,203,841 A * | 4/1993 | Kitabayashi | ......... | B65D 47/305 |
| | | | | 222/402.11 |
| 6,325,304 B1 * | 12/2001 | Brite | ................ | A01M 7/0046 |
| | | | | 239/333 |
| 6,543,653 B2 * | 4/2003 | Lamboux | ............ | B05B 11/3009 |
| | | | | 222/321.8 |
| 6,601,735 B2 * | 8/2003 | Milian | ................ | B05B 11/0027 |
| | | | | 222/153.11 |
| 7,784,650 B2 * | 8/2010 | Bates | ................ | B65D 83/202 |
| | | | | 222/402.13 |
| 8,978,936 B2 * | 3/2015 | Eini | ................ | B65D 83/682 |
| | | | | 222/402.1 |
| 9,738,436 B2 * | 8/2017 | Sell | ................ | B65D 83/206 |
| 10,064,472 B2 * | 9/2018 | Campbell | ............ | A45D 34/00 |
| 10,647,501 B2 * | 5/2020 | Richard | ............... | B65D 83/206 |
| 11,034,507 B2 * | 6/2021 | Spang, Jr. | ............ | B65D 83/206 |
| 2005/0103892 A1 * | 5/2005 | Rohrschneider | ....... | B65D 83/20 |
| | | | | 239/337 |
| 2009/0084870 A1 * | 4/2009 | Smith | .................. | B65D 83/753 |
| | | | | 239/303 |
| 2009/0214994 A1 * | 8/2009 | Gdynia | .................... | F23Q 2/16 |
| | | | | 431/77 |
| 2010/0042087 A1 | 2/2010 | Goldboss et al. | | |
| 2010/0059551 A1 | 3/2010 | Tomkins et al. | | |
| 2010/0147898 A1 * | 6/2010 | Blumenstein | ....... | B29C 45/1657 |
| | | | | 222/402.13 |
| 2011/0132936 A1 * | 6/2011 | Weng | .................. | B65D 83/201 |
| | | | | 222/402.13 |
| 2011/0233235 A1 * | 9/2011 | Adams | ................. | B65D 83/205 |
| | | | | 222/402.13 |
| 2013/0001323 A1 | 1/2013 | Bodet et al. | | |
| 2013/0008540 A1 * | 1/2013 | Shah | .................... | B05B 1/3426 |
| | | | | 137/808 |
| 2014/0110440 A1 | 4/2014 | Good et al. | | |
| 2014/0361049 A1 * | 12/2014 | Arora | .................... | B65D 83/206 |
| | | | | 222/402.11 |
| 2015/0375921 A1 * | 12/2015 | Sell | ....................... | B65D 83/206 |
| | | | | 222/153.11 |
| 2016/0347533 A1 * | 12/2016 | Giordano | ............... | A45D 27/10 |
| 2019/0031426 A1 * | 1/2019 | Schroer | ............... | B65D 83/303 |
| 2019/0308797 A1 * | 10/2019 | Schroer | ............... | B65D 83/306 |
| 2019/0308798 A1 * | 10/2019 | Schroer | .................. | B65D 83/30 |
| 2019/0315558 A1 * | 10/2019 | Ehrensperger | ......... | B65D 83/22 |
| 2020/0062489 A1 * | 2/2020 | Spang, Jr. | ............ | B65D 83/206 |
| 2020/0180847 A1 * | 6/2020 | Schroer | ............... | B65D 83/303 |
| 2021/0261320 A1 * | 8/2021 | Spang, Jr. | ............ | B65D 83/206 |

FOREIGN PATENT DOCUMENTS

| | | |
|---|---|---|
| WO | WO 2010/041411 A1 | 4/2010 |
| WO | WO 2012/007843 A2 | 1/2012 |
| WO | WO 2016/163987 A1 | 10/2016 |

\* cited by examiner

AEROSOL DISPENSERS AND CONTAINERS AND HEADS FOR SUCH CONTAINERS

This application is a 35 U.S.C. 371 filing of International Application No. PCT/EP2017/084401, filed on Dec. 22, 2017, which claims priority to and the benefit of European Patent Application EP 16206663.3 filed on Dec. 23, 2016, all of which are incorporated verbatim herein by reference in their entirety, including the specifications, drawings, and the claims.

The present disclosure relates to aerosol dispensers and aerosol containers, particularly to heads or tops for aerosol containers. More particularly, the present disclosure relates to aerosol dispensers and containers for use in cryotherapy.

BACKGROUND

Post-infection topical treatments are usually used to treat skin warts occurring on the sole or toes of the foot and/or other varieties of warts or other skin diseases. From these topical treatments cryotherapy is well-known.

Cryotherapy is usually used in the medical field for the removal of skin lesions formed in the body of mammals, including the human body. Cryotherapy refers to treatments in which surface skin lesions are frozen. However, cryotherapy may sting and may be painful, both when being performed and for a variable period afterwards. In circumstances, the extreme cold can freeze blood vessels supplying blood to abnormal cells.

Some known cryotherapy techniques combine the effectiveness of traditional cryotherapy with a modern aerosol technique. This involves rather simple and user-friendly treatment devices. In these techniques, the coolant solution is usually stored in a pressurized container and, upon demand an amount of coolant solution is dispensed from the container.

One known aerosol container comprises norflurane. Norflurane is also known as HFC-134A, and has a chemical structure known as 1,1,1,2-tetrafluoroethane. Aerosol cans containing 1,1,1,2-tetrafluoroethane, when inverted, become effective freeze sprays. Under pressure, 1,1,1,2-tetrafluoroethane is compressed into a liquid, which upon vaporization absorbs a significant amount of thermal energy. As a result, it will greatly lower the temperature of any object it contacts as it evaporates, i.e. in this case the skin lesions or warts.

To control the amount of coolant solution dispensed onto the skin, some devices involve delivering metered doses. Document US2010042087 describes such devices.

This reduces the amount of coolant solution that may be wasted in these treatments but it does not control spraying or splashing outside the intended treatment area or even the hands of the user. To reduce spraying outside the intended treatment area document US2010042087 provides different applicator's head adapted to different applications.

Document WO2016/163987 discloses dispensing systems involving an overcap including housing. The housing has a first side wall including an aperture. The overcap further includes a trigger having a grip portion disposed outside of the housing and an arm extending through the aperture of the first side wall and pivotally coupled to a fulcrum spaced apart from the first side wall. The overcap also includes a cap coupled to the housing and a manifold suspended from the cap.

Document US20100059551 discloses an aerosol sprayer including an actuator attached to the container. The actuator includes a housing and a trigger piece having a trigger and operatively associated with the housing to activate the release of fluid from the container. The actuator further includes a nozzle in fluid communication with the container and a trigger loop encircling the trigger.

However, there is a continuing need for providing high accuracy devices that may be used by a wide range of users with various backgrounds and training levels and that reduce the risk of damaging the skin next to the skin lesion being treated. There is also a need for reducing waste of the active product in an aerosol container.

Examples of devices and methods of the present fulfill one or more of these needs at least partially.

SUMMARY

In a first aspect, a head for an aerosol container is provided. The aerosol container includes a valve assembly that comprises a container exit and a valve body for selectively opening a passage from an interior of the aerosol container to the container exit. The head comprises a handle body having a base configured to be coupled to the aerosol container, and a spray outlet. The head also comprises a flexible tube housed within the handle body. The flexible tube is configured to provide fluid communication between the container exit and the spray outlet. And the head further comprises an elastically deformable actuator that comprises a lever arm, and a coupling portion integrally formed with the lever arm and configured to be mounted around the flexible tube, the container exit and a portion of the valve body. The coupling portion is further configured such that when the lever arm is deformed by a user, the coupling portion actuates on the valve body of the aerosol container.

According to this aspect, elastic deformation of the lever arm produces a downwards deformation/movement of the coupling portion that is mounted around the valve body thereby pressing directly (or indirectly) on the valve body such that the propellant and the active ingredient housed within the aerosol container flow out the container exit and through the flexible tube towards the outlet. When this occurs, the provision of a flexible tube connecting the container exit with the outlet ensures the fluid communication between the container exit and the outlet when the valve assembly is actuated by the coupling portion. At the same time, the fact that the outlet forms part of the handle body and is separately built with respect to both, the elastically deformable actuator and the flexible tube guarantee that the outlet does not move when the coupling portion is deformed to actuate the valve body. According to this aspect, actuation of the valve by the elastically deformable actuator together with the fact that the tube is flexible makes it possible to maintain fluid communication between the container exit and the spray outlet during actuation of the valve body by deformation of the coupling portion. And this is done while maintaining the outlet fixed (immobile).

Put in other words, the outlet does not move when the aerosol valve assembly is actuated, which enhances accuracy of the spraying.

Further in this aspect, the fact that the elastically deformable actuator comprises a lever arm provides for an easy handling of the head by the user, both for highly experienced and entry level health practitioners.

In some examples, the coupling portion may have a stepped shape for acting on the valve body.

In some examples, the spray outlet may be integrally formed with the handle body. This further contributes to ensure that the outlet does not move as a consequence of actuating the elastically deformable actuator thereby acting the aerosol valve.

In some examples, the head may further comprise an extension tube configured to be coupled to spray outlet and extend away from the handle body. This way an area of application may be provided farther away from the handle body, and thus from the hands of the user. This contributes to reduce accidentally spraying on the hands of the user and it can facilitate application of the composition in less accessible areas e.g. inside the mouth of a patient. In some of these examples, the extension may be discarded after use with one patient or one treatment area. Alternatively, it may be reusable by removing the extension tube from the flexible tube and then having it sterilized after each use. This can improve safety of the application as it reduces contamination of the head.

In some of these examples, a nozzle may be provided at a distal end of the extension tube. In these cases, the nozzle may comprise an inner through channel. The inner through channel may in turn comprise two or more sections of different diameters. Sections of different diameters may be connected to each other with a conical shaped connector. This refines the spraying as having a change in the inner diameter varies the speed and pressure of a fluid flowing through the nozzle. A concentrated spray can be provided rather than a dispersed cloud of spray which is provided by some prior art devices.

In addition, the provision of a nozzle substantially as hereinbefore described also contributes to prevent dripping.

In some examples, the head may further comprise a disc rotatably provided at the base. The disc may be provided with two or more steps configured to limit movement of the coupling portion. The steps may have different heights such that different steps define different levels of actuation of the valve assembly. In these cases, the coupling portion may be provided with a downwards protrusion configured to make contact with the steps of the disc when the coupling portion is deformed such that the different levels of actuation of the valve assembly are defined by rotating the disc such that the protrusion makes contact with a different step when the lever is actuated by the user and the coupling portion is moved or deformed. This way, downwards deformation/movement of the coupling portion is limited which in turn limits spraying intensity by controlling the opening of the valve of the aerosol container.

The steps may particularly be different "axial" steps, i.e. the steps can have different heights in the axial direction (the axial direction being parallel to the longitudinal axis of the aerosol container).

In some of these examples, one of the steps may be a security step configured to make contact with the protrusion of the coupling portion before the lever arm is deformed by a user such that deformation of the actuator is impeded. The security step thus provides a security measure that blocks or prevents actuation of the valve of the aerosol container when it is not desired.

In another aspect, an aerosol container is provided. The aerosol container comprises a valve assembly that comprises a container exit and a valve body for selectively opening a passage from an interior of the aerosol container to the container exit. The aerosol container further comprises a head substantially as hereinbefore described.

In some examples, the aerosol container may include a therapeutic or prophylactic composition comprising an active ingredient and a pressurized liquid propellant. Particularly examples wherein the active ingredient may be a cryotherapy active ingredient may be foreseen. And more particularly, in some implementations the aerosol container may contain norflurane as active ingredient as well as propellant.

In yet further examples, the composition may comprise liquid nitrogen as active ingredient and propellant. In further alternatives, compositions comprising dimethyl ether, propane and/or isobutene may be foreseen.

In still another aspect, a kit for treatment of skin lesions may be provided. The kit comprises a head for an aerosol container substantially according to any of the examples as hereinbefore described and a plurality of extension tubes of different diameters and/or lengths. Different lengths and/or diameters may be foreseen for different applications such as treating different skin lesions and or different degrees of lesions or different types of skin, including applications in adults and/or children and different body parts. Particularly, kits for cryotherapy of skin lesions may be foreseen.

In some examples, the kit may further comprise a plurality of application templates comprising a surface and a plurality of holes of different sizes. Optionally, such a template may have a gripping portion of increased roughness for easy handling. The roughness may be provided e.g. by having consecutive raised and depressed areas. The templates may also contribute to reduce spraying outside the targeted skin segment.

Heads for aerosol containers, aerosol containers including such heads and kits substantially as hereinbefore described are not only used in cryotherapy. Instead they may also be used for prophylactic or cosmetic treatments, or even in other non-medical applications using spraying with aerosol containers such as e.g. painting.

BRIEF DESCRIPTION OF THE DRAWINGS

Non-limiting examples of the present disclosure will be described in the following, with reference to the appended drawings, in which.

DETAILED DESCRIPTION OF EXAMPLES

In these figures the same reference signs have been used to designate matching elements.

Figure 1:
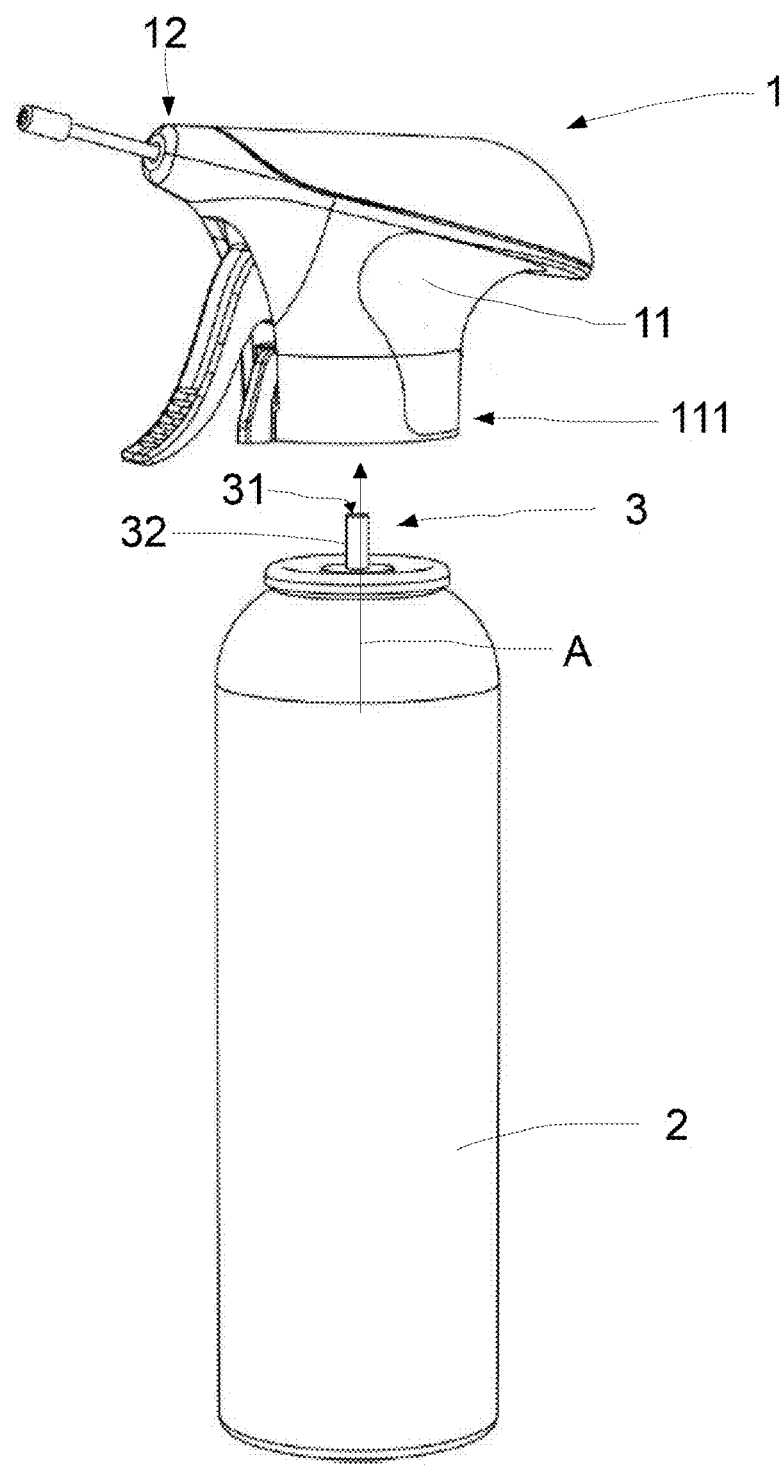
FIG. 1 shows a perspective of an aerosol container with a head according to an example.

FIG. 1 shows a perspective of an example of an aerosol container 2 with a head 1. The head 1 is configured to be coupled to the aerosol container 2.

The aerosol container 2 comprises a valve assembly 3 that includes a container exit 31 and a valve body 32 for selectively opening a passage (arrow A) from an interior of the aerosol container to the container exit 31. The valve body 32 depicted here may be an actuator that is displaced and directly provides a passage from the interior of the container to the outside. Depending on the valve used, the valve body may instead act on the actuator. In the particular example shown in FIG. 1, the valve body 32 may be a stem that is pressed upwards (to a closed position) by a spring. Below the valve body shown, a so-called dip tube may be provided. Upon moving the valve body 32 (in this case, the stem) downwards, the spring may be compressed and a passage from a dip tube towards the container exit 31 may be opened.

It should be clear that within the scope of the present disclosure, different types of valves and valve mechanisms may be used.

The head 1 comprises a handle body 11 and a spray outlet 12. The handle body 11 has a base 111 that is configured to be coupled to the aerosol container 2, for example, by snap-fitting. Other ways of coupling the head to the container may be foreseen. In this example, the handle body 11 comprises an ergonomically outer shape which facilitates handling by a user.

Figure 2:
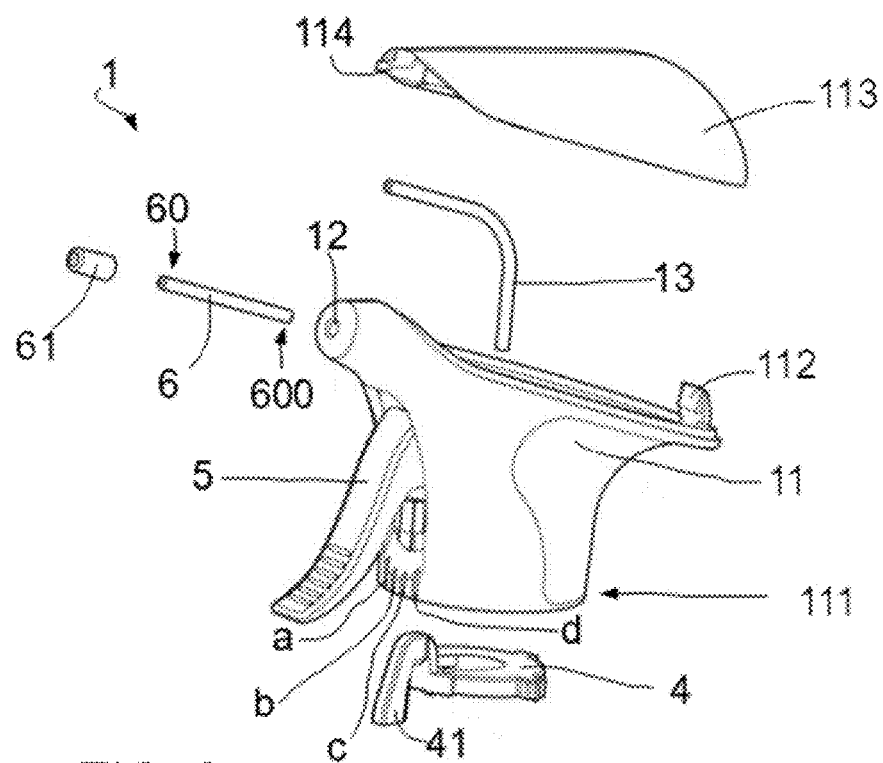
FIG. 2 shows an exploded view of the head of FIG. 1.

FIG. 2 shows an exploded view of the head 1 of FIG. 1. According to this example, the handle body 11 comprises a top flange 112 configured to removably mount a handle top 113 that is provided with a corresponding matching indentation (not shown) for an interlock coupling with the handle body 11. In addition, the handle top 113 is provided with a forward flange 114 configured to removably mount the handle top 113 to the handle body 11, and the handle body 11 comprises a matching indentation (not shown) for another interlock coupling. Other ways of mechanically coupling these two portions forming the handle body may be foreseen. Alternatively the handle body may be made in one piece. An aspect of having an openable handle top is that it may facilitate assembly.

As further shown in FIG. 2, a flexible tube 13 is housed inside the handle body 11, a lever arm 5 forming part of an elastically deformable actuator is also housed inside the handle body 11 and protrudes out from the handle body 11. A disc 4 is further housed inside the handle body 11, in correspondence with the base 111 of the handle body 11. The disc 4 comprises an extension 41 for handling by a user.

Furthermore, the base 111 is provided with four protrusions or marker lines a, b, c and d configured to indicate different positions/orientations of the extension 41 with respect to the handle body 11, and optionally may engage the extension 41 of the disc 4. Alternatively other number of protrusions and alternative markers or marker lines may be foreseen.

An extension tube 6 is configured to be coupled inside the spray outlet 12 and a nozzle 61 is mountable to a distal end 60 of the extension tube 6.

Figure 3:
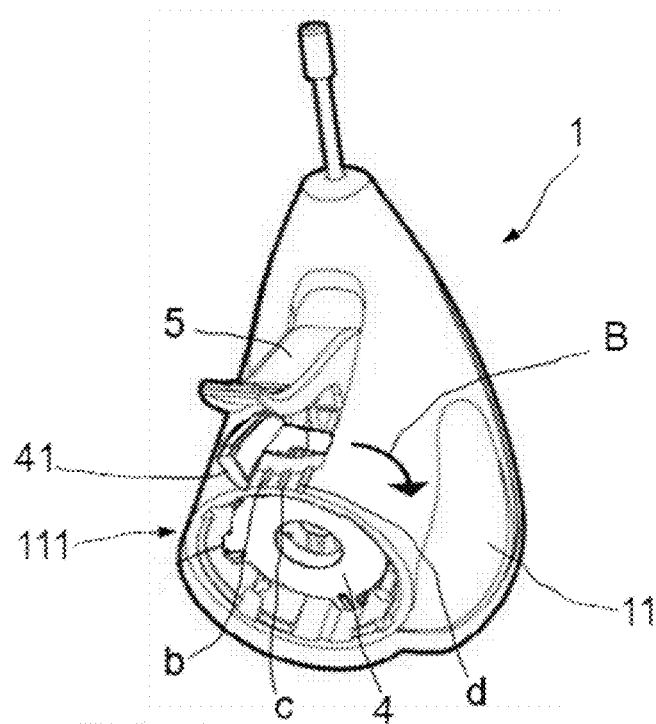
FIG. 3 shows a perspective viewed from below of the head of FIG. 2.

FIG. 3 shows a bottom view of the head 1. According to this figure, the disc 4 is rotatably mounted inside the base 111 of the handle body 11. And the extension 41 of disc 4 touches on protrusion a (not visible). As further shown in this example, protrusions b, c and d are configured to engage the extension 41 of the disc 4 at different operational positions upon rotation of the disc 4 along direction of arrow B. Rotating the disc is a manual action a user might do before actuating on the lever arm. To rotate the disc, the user thus merely needs to manually move the extension 41 to engage the desired protrusion a-d of the base 111.

Figure 4A:
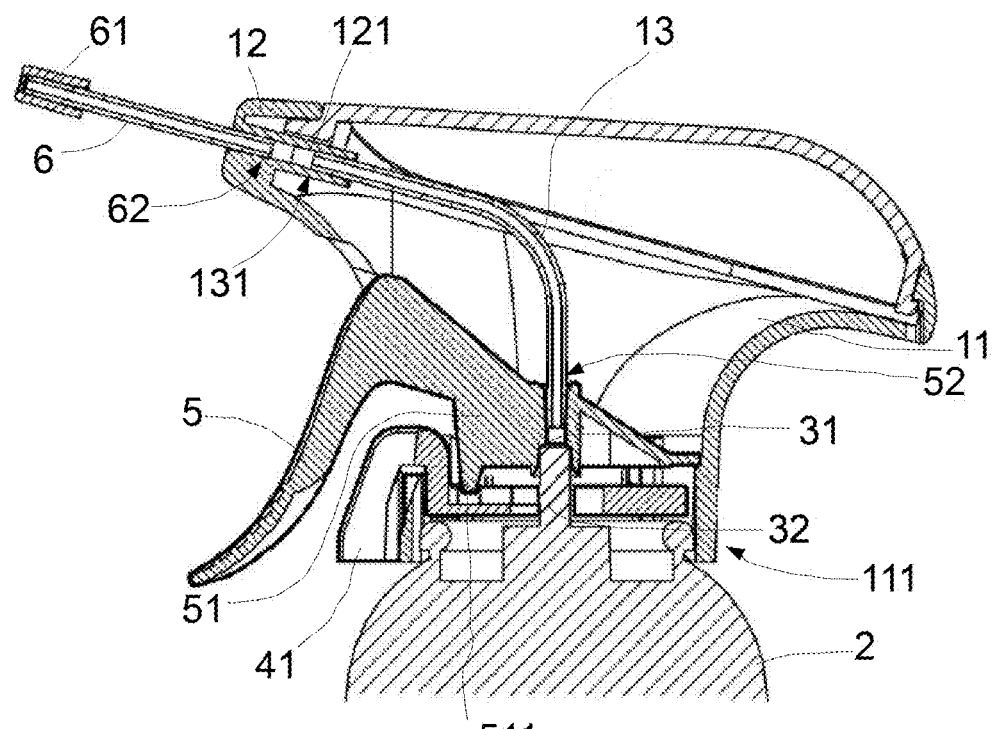
FIGS. 4*a* and 4*b* show cross-sectional views of the head of FIG. 2 in two states.
Figure 4B:
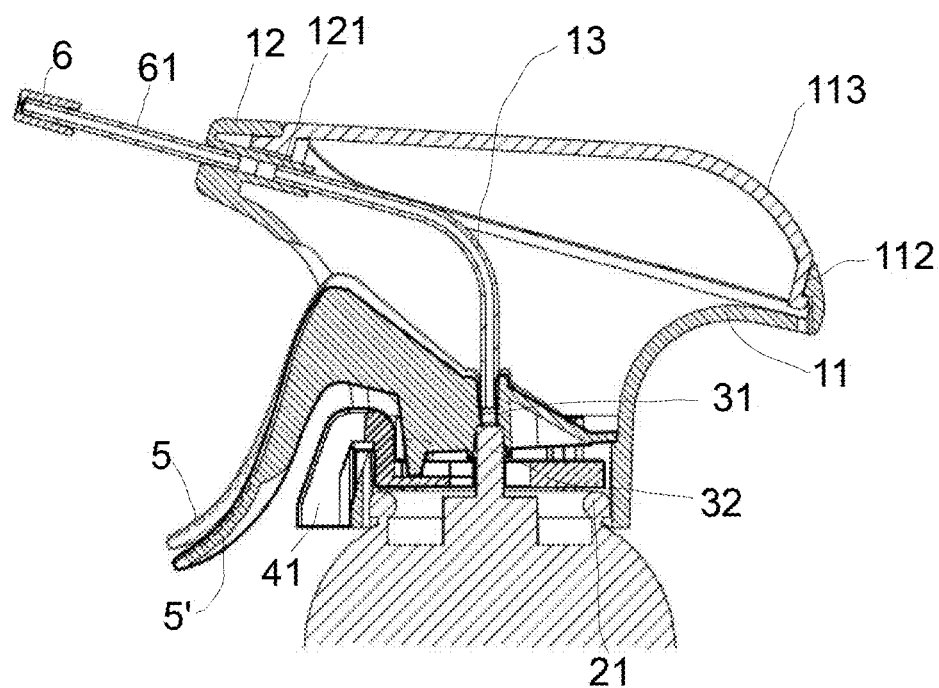

FIGS. 4a and 4b show cross-sectional views of a head substantially as hereinbefore described in two different states. FIG. 4a shows a rest state, i.e. a state in which no force is applied to the lever arm 5 and FIG. 4b shows a spraying state in which a user applies a force on the lever arm 5.

According to these examples, the flexible tube 13 housed inside the handle body 11 is configured to provide fluid communication between the container exit 31 of the aerosol container 2 and the outlet 12. To do this, the outlet 12 is provided with an inner passage 121 configured to receive a distal end 131 of the flexible tube 13. Within such an inner passage 121 the outlet 12 is further configured to receive a proximal end 600 of the extension tube 6. In alternatives, no extension tube may be provided and thus the inner passage 121 provides an exit for the contents of the container 2.

In the example of FIGS. 4a and 4b, a proximal end 600 of the extension tube 6 and the distal end 131 of the flexible tube 13 are configured to be connected to each other inside the inner passage 121 of the outlet 12. And a distal end of the extension tube 6 is provided with a nozzle 61 as will be explained in connection with FIG. 6. In examples, other types of nozzles may be used, e.g. as will be explained in connection with FIG. 9.

As further shown in FIGS. 4a and 4b, the lever arm 5 is integrally formed with a coupling portion 51 to form the elastically deformable actuator. The coupling portion 51 is partially housed inside the handle body 11 and comprises a through-hole 52 for being mounted around the flexible tube 13, the container exit 31 and a portion of the valve body 32. This way, when the lever arm 5 is deformed by a user, the coupling portion 51 deforms downwards and actuates on the valve body 32 thereby opening the container exit 31 and releasing the content of the aerosol container 2.

Particularly in these examples, the coupling portion 51 is provided with a downwards protrusion 511 configured to make contact with the disc 4 as will be explained in connection with FIG. 5.

In FIG. 4b a force is applied by a user on the lever arm 5' that moves from its position in FIG. 4a (lever arm 5) towards the extension 41 of the disc 4 and as it is integrally formed with the coupling portion 51, and is made from an elastically deformable material, such a force applied on the lever arm 5' makes the coupling portion 51 deform/move downwards towards and press down the valve body 32 thereby opening the container exit 31 and releasing the content of the container 2 through the container exit 31 and the flexible tube 13. The content of the container flows towards the inner passage 121 of the outlet 12 and through the extension tube 6 onto the target skin segment, e.g. a skin lesion.

As shown in these figures, the only movable parts are thus the actuator assembly formed by the lever arm 5 and the coupling portion 51 and the valve body 32. The flexible tube 13 is deformed by the deformed coupling portion 51 and at the same time the flexible tube 13 allows the passage of the content of the container. This is done, without moving the handle body 11 thereby not moving the outlet 12 or its inner passage 121. Since the content of the container exits through the outlet 12 (or the extension tube 6 coupled to the outlet 12), the opening through which the content of the container exits as such does not move. This enhances accuracy of spraying.

In alternative examples, the head may be provided without a disc substantially as hereinbefore described.

FIGS. 4a and 4b further show that the base 111 of the head 1 is snap-fitted on a flange 21 of the container. Other ways of coupling the head to the container may be foreseen, e.g. matching threads.

Figure 5:
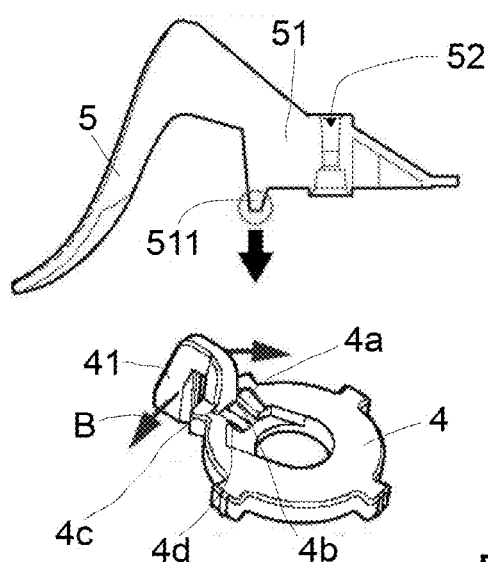
FIG. 5 shows details of an elastically deformable actuator and a disc according to an example.

FIG. 5 shows further details of the disc 4 and an example of how deformation or movement of the coupling portion 51 may be limited by the disc 4. In this example, the disc 4 comprises four steps 4a-4d having different axial heights. As shown in this example, the coupling portion 51 comprises a downwards protrusion 511 configured to make contact with any of the steps 4a-4d. This way, the lever arm 5 is configured to be actuated by a user until the downwards protrusion hits on one of the steps 4a-4b. This means that each step 4a-4d provides a limit to the downwards movement allowed to the coupling portion 51 which in turn provides a limit to the stroke that a user can make on the lever arm 5.

In these examples, to define a different level of actuation of the valve assembly, i.e. to provide different spraying intensities, the disc 4 is rotated (see arrow B) such that the extension 41 of the disc 4 is engaged in a different protrusion a, b, c and d of the base 111.

In examples, step 4a is configured as a security step. The security step is high enough to effectively avoid any movement of the lever arm 5. In these examples, the downwards protrusion 511 of the coupling portion 51 is in contact with step 4a when the lever arm 5 is not actuated, i.e. in the rest state shown in FIG. 4a. This provides a safety measure for the head 1.

In alternative examples, other number of steps substantially as explained in connection with FIG. 5 may be foreseen, including examples in which the disc only involves a single step such as a security step substantially as that referred to as numeric reference 4a in FIG. 5. Additionally, examples in which the disc may have the security step and a single "working step" substantially as any of the steps referred to as numeric references 4b-4d in FIG. 5. This simplifies operation of the head.

Figure 6:
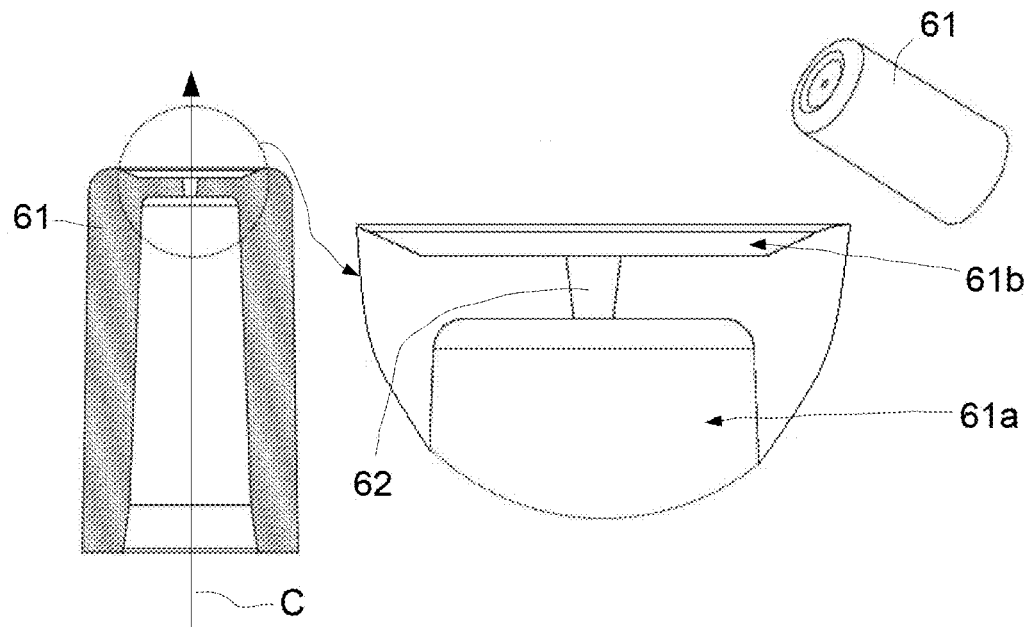
FIG. 6 shows perspective and cross-sectional views of a nozzle according to an example.

FIG. 6 shows details of the nozzle 61 substantially as hereinbefore described. In this example, the nozzle 61 comprises an inner through channel (see arrow C) comprising two sections 61a and 61b having inner diameters of different sizes. Alternative other number of sections may be foreseen. Particularly the inner diameter of section 61a is slightly smaller than the inner diameter of section 61b. And the sections 61a and 61b are connected to each other with a conical shaped connector 62. Particularly, as further shown in the enlarged detail of FIG. 6, an inner diameter of section 61b comprises a variable diameter that increases distally from the head. This reduces dripping at a distal end of the nozzle.

The fluid that exits the aerosol container thus first passes from a first diameter of section 61a to a channel with a much smaller diameter at the entrance of the conical connector 62. The diameter at the entrance of the connector 62 may be 4-8 times smaller than the diameter of section 61a. The connector 62 slightly tapers outwardly, towards the exit. The section 61b at the exit has a diameter that is much larger, e.g. 4-8 times larger than the diameter at the exit of the connector 62. Particularly, section 61a slightly tapers distally, towards connector 62.

In a particular example, a nozzle 61 having a total length of approximately 8.10 mm and an outer diameter of approximately 4.55 mm may be used, having the following (internal) dimensions: section 61a having a length of approximately 7.5 mm, connector 62 having a length of approximately 0.4 mm and section 61b having a length of approximately 0.2 mm. In this particular example shown, section 61a comprises a most proximal tapered portion having a length of approximately 1 mm and an intermediate tapered portion having a length of approximately 6.5 mm. The most proximal tapered portion has an inner diameter starting at approximately 2.85 mm and ending at approximately 2.57 mm and the intermediate tapered portion has an inner diameter starting approximately 2.57 mm and ending at approximately 2.05 mm. Section 61a, at its most proximal end, has a short curved portion leading towards the connector 62. The connector 62 has an inner diameter starting (the proximal end of the connector) at approximately 0.25 mm and ending at approximately 0.35 mm at the distal end of the connector leading to section 61b.

In examples, the handle body, the handle top and/or the disc may be made e.g. from a high-density polyethylene (HDPE) such as Rigidex® HD 5211 EAB, commercially available from BP Solvay Polyethylene. The flexible tube and/or the extension tube may be made from another high-density polyethylene (HDPE) such as RB82. The nozzle may be made e.g. from a polyozymethylene (polyacetal, POM) such as Hostaform® C27021XAP, commercially available from Resinex. And the aerosol container or canister may be made from aluminum.

Figure 7:
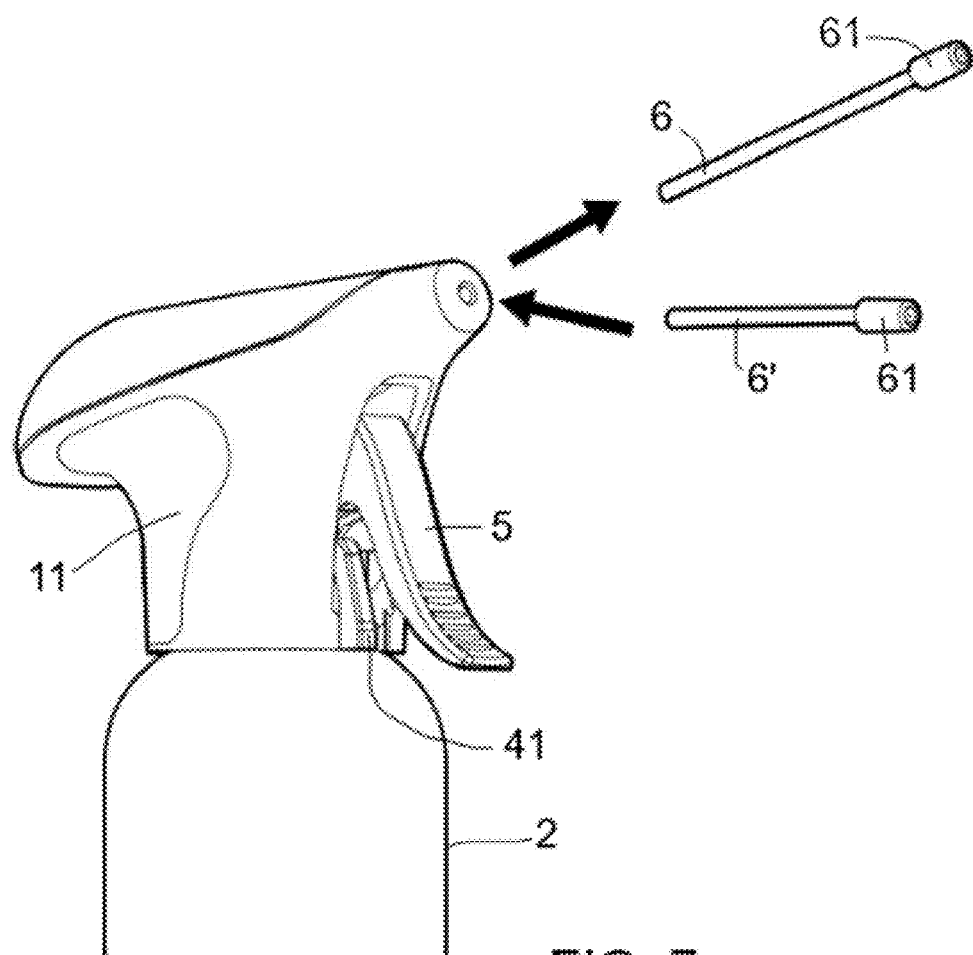
FIG. 7 shows a kit according to an example.

FIG. 7 shows a kit for treatment of skin lesions comprising a head substantially as hereinbefore and a further extension tube 6' whose distal end is provided with a nozzle 61 substantially as hereinbefore described. Extension tube 6' has a different length and/or diameter than extension tube 6. The kit is thus more versatile than just a head and container substantially as hereinbefore described as tubes of different length and/or diameters can be used for different applications, for example, for different skin lesions and/or different treatments in general such as skin warts or dentist appliances among others. These examples may also be combined with other types of nozzles, e.g. the nozzle 61' that will be explained in connection with FIG. 9.

In some examples, norflurane which is a well-known propellant used in several asthma inhalers may be foreseen.

Figure 8:
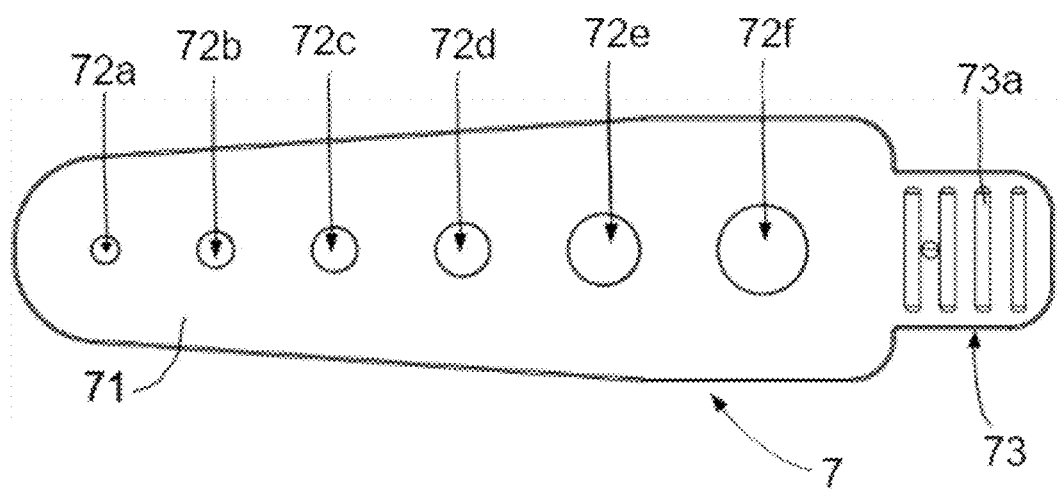
FIG. 8 shows an application template according to an example.

FIG. 8 shows an application template according to an example. The application template 7 may be used with an aerosol container having a head substantially as hereinbefore described. In this example, the application template 7 has a surface 71 provided with six holes 72a-72f. Alternatively other number of holes may be foreseen including a single hole. In the template 7 of FIG. 8, the holes 72a-72f have a circular shape having different diameters. In an example, the diameters may be 3, 4, 5, 6, 8 and 10 mm, respectively. A user might determine the size of the lesion by using the template 72. An instruction for use leaflet may be included with the product explaining to the user which actions to take depending on the size of the lesion. For example, depending on the size of the lesion, a specific extension tube may be prescribed. In a further example, depending on the size of the lesion, it might be prescribed to rotate disc 4 to a predetermined orientation.

In addition, as further shown in the example of FIG. 8, examples of the template 7 may comprise a gripping portion 73 at one end to provide for a safe and secure handling of the template. In examples, the gripping portion 73 has a gripping surface with substantially parallel raised and depressed areas 73a. In alternatives, different raised and depressed configurations or other forms of roughening or wrinkling may be foreseen for defining a suitable gripping area.

Other diameters may be foreseen in a template substantially as hereinbefore described. In more alternatives, holes of other shapes or combination of shapes may also be foreseen. To reduce the risk of infection, the application templates may be single-use templates. The templates may be discarded as regular household waste after use.

Figure 9:
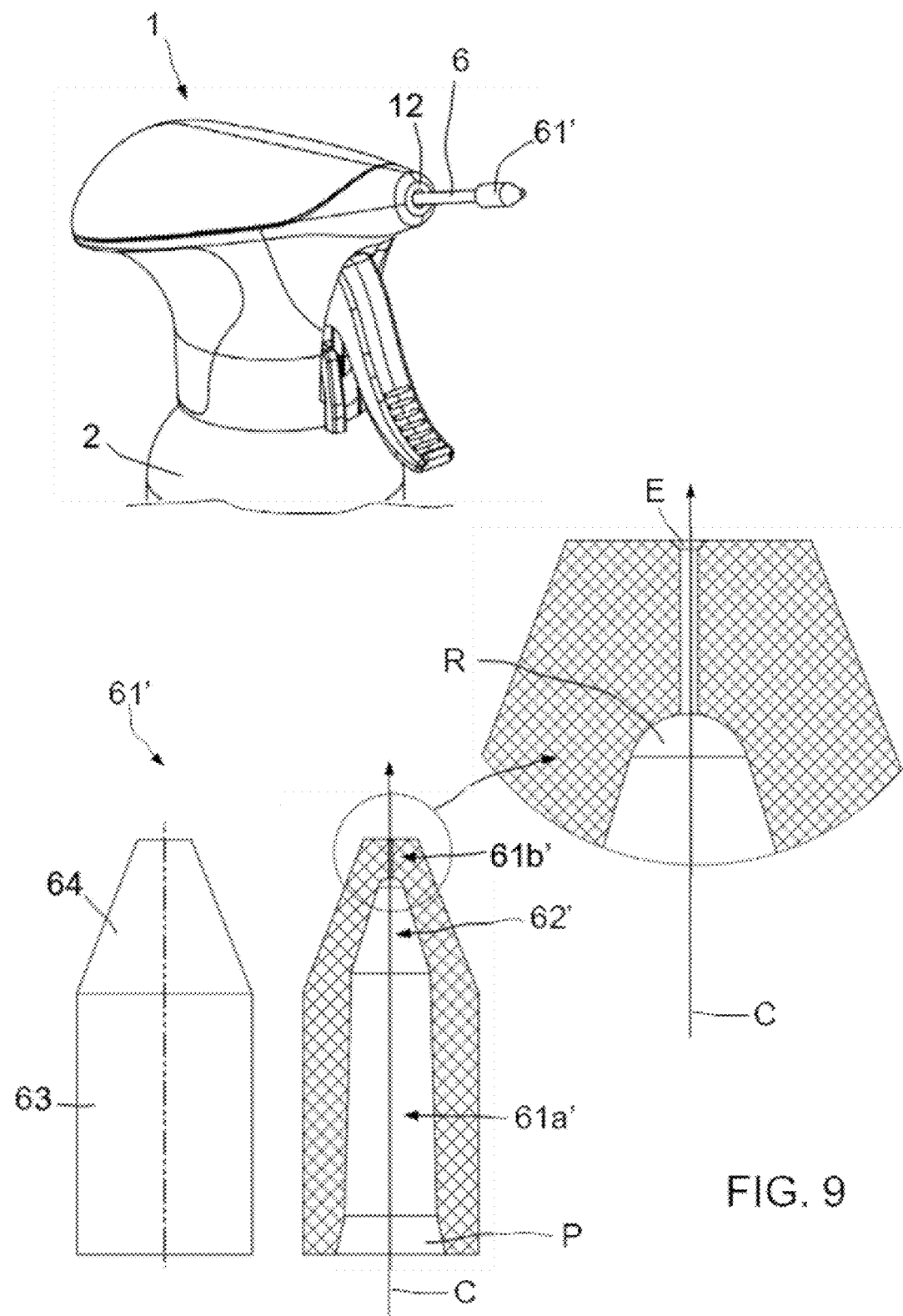
FIG. 9 shows a nozzle according to another example mounted in the head of FIGS. 1-4*b*.

FIG. 9 shows a perspective of a head substantially as hereinbefore described in combination with an extension tube 6 and another type of nozzle 61'. The nozzle 61' described in the example of FIG. 9 differs from that of FIG. 6 at least in its outer shape. In this example, an outer shape of the nozzle 61' comprises two well-defined portions: a cylindrical portion 63 that in use is proximally mounted with respect to the outlet 12 and a consecutive conical portion 64 tapering distally when mounted on the extension tube 6. Further in this example, the conical portion 64 is truncated.

As shown in the cross-sectional view, nozzle 61' comprises an inner through channel (see arrow C) comprising two sections 61a' and 61b' having inner diameters of different sizes, sections 61a' and 61b' being connected to each other with a conical shaped connector 62' substantially as explained with respect to the nozzle 61 described in the example of FIG. 6. The nozzle 61' described in the example of FIG. 9 further differs from that of FIG. 6 in the relative inner shapes of the sections 61a', 61b' and of the conical shaped connector 62'.

Particularly in this example, an inner diameter of section 61a' is much bigger than an inner diameter of section 61b', e.g. approximately 24 times bigger. Further in this example, the conical shaped connector 62' tapers from section 61a' to section 61b'. Moreover, the enlarged detail shows that the conical shaped connector 62' ends in a rounded shaped end portion R having a diameter which is approximately 3 to 4 times smaller than the inner diameter of section 61a'; and the inner diameter of section 61b' which in this example has a straight conical shape, is about 7 times smaller than that of the rounded shaped end portion R.

In addition, the inner diameter of section 61a' comprises a proximal portion P having a variable diameter that decreases distally when in use (mounted on the extension tube). And section 61b' at its exist E has a slightly tapered outwardly portion having an enlarging diameter ending in a diameter that is e.g. 2 times larger than that of the inner diameter of section 61b'. This reduces dripping at a distal end of the nozzle 61'.

The fluid that exits the aerosol container thus first passes from a first diameter of the proximal portion P to a smaller diameter of section 61a' and an entrance of the conical shaped portion 62'. Then it traverses to a much smaller diameter at the entrance of section 61b' and it exits through the tapering outwardly portion E.

In a particular example, a nozzle 61' having a total length of approximately 10.80 mm and an outer diameter (at least at the cylindrical portion 63) of approximately 4.55 mm may be used. An outer diameter of an end of the conical portion 64 may be approximately 1.40 mm. In this example, the following inner dimensions may be foreseen: section 61a' may have a length of approximately 6.8 mm, connector 62' may have a length of approximately 3.8 mm and section 61b' may have a length of approximately 1 mm. In this particular example, section 61a' in turn may have a most proximal tapered portion P having a length of approximately 1 mm. The most proximal tapered portion P may have an inner diameter starting at approximately 2.85 mm and ending at approximately 2.40 mm and the inner diameter of section 61a' may be approximately 2.40 mm. The connector 62' may have an inner diameter starting (the proximal end of the connector) at approximately 2.40 mm and ending at approximately 0.70 mm at the distal rounded end R (radius of about 0.35 mm) leading to section 61b'. Section 61b' may have an inner diameter of approximately 0.10 mm increasing distally towards exit E having a diameter of approximately 0.20 mm.

Examples of nozzles as explained in connection with FIG. 6, i.e. having a substantial cylindrical outer shape are particularly adequate for treating warts, skin lesions and/or mucosal lesions with considerable areas. Examples of nozzles as explained in connection with FIG. 9, i.e. having a conical tip are particularly adequate for target lesions in sensitive anatomical location as such as e.g. the face and/or genitals.

In all examples substantially as hereinbefore described, nozzle 61 as shown in FIG. 6 may be replaced by nozzle 61' as shown in FIG. 9.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A head for an aerosol container including a valve assembly, the valve assembly comprising a container exit and a valve body for selectively opening a passage from an interior of the aerosol container to the container exit, the head comprising:
   a handle body having a base configured to be coupled to the aerosol container, and an outlet;
   a flexible tube housed within the handle body, the flexible tube being configured to provide fluid communication between the container exit and the outlet,
   a disc rotatably provided at the base, and
   an elastically deformable actuator comprising
      a lever arm, and
      a coupling portion integrally formed with the lever arm and configured to be mounted around the flexible tube, the container exit and a portion of the valve body, the coupling portion being further configured such that when the lever arm is deformed by a user, the coupling portion actuates the valve body of the aerosol container, and
   the disc being provided with two or more steps configured to limit elastic deformation of the coupling portion, the steps having different heights such that different steps define different levels of actuation of the valve assembly and wherein
   the coupling portion is provided with a downwards protrusion configured to make contact with the steps of the disc when the coupling portion is deformed such that the different levels of actuation of the valve assembly are defined by rotating the disc such that the protrusion makes contact with a different step when the coupling portion is deformed.

2. The head of claim 1, wherein the coupling portion is provided with a through-hole for being mounted around the flexible tube, the container exit and a portion of the valve body.

3. The head of claim 1, wherein the outlet is integrally formed with the handle body.

4. The head of claim 1, wherein a distal end of the flexible tube is attached to the outlet.

5. The head of claim 4, wherein the outlet is provided with an inner passage configured to receive the distal end of the flexible tube.

6. The head of claim 1, further comprising an extension tube configured to be coupled to the outlet.

7. The head of claim 6, further comprising a nozzle provided at a distal end of the extension tube, wherein the nozzle comprises an inner through channel, the inner through channel comprising two or more sections of different diameters, the sections of different diameters being connected to each other with a conical shaped connector.

8. The head of claim 1, wherein one of the steps is a security step configured to make contact with the protrusion of the coupling portion before the lever arm is deformed by a user such that deformation is impeded.

9. The head of claim 1, wherein the handle body has an ergonomically outer shape.

10. The head of claim 1, further comprising a handle top configured to match with an upper part of the handle body.

11. A kit for treatment of skin lesions comprising the head for an aerosol container according to claim 1 and a plurality of extension tubes having different diameters and/or different lengths.

12. The kit of claim 11, further comprising a plurality of application templates, the templates comprising a surface and a plurality of holes of different sizes.

13. A device comprising:
an aerosol container including a valve assembly, and
a head,
wherein the valve assembly comprises an exit of the aerosol container and a valve body for selectively opening a passage from an interior of the aerosol container to the exit of the aerosol container, and the head comprising:
a handle body having a base configured to be coupled to the aerosol container, and an outlet;
a flexible tube housed within the handle body, the flexible tube being configured to provide fluid communication between the exit of the aerosol container and the outlet;
disc rotatably provided at the base; and
an elastically deformable actuator comprising
a lever arm, and
a coupling portion integrally formed with the lever arm and configured to be mounted around the flexible tube, the container exit and a portion of the valve body, wherein
the coupling portion is configured such that when the lever arm is deformed by a user, the coupling portion acts on the valve body to open the passage from the interior of the aerosol container to the exit of the aerosol container and to the outlet, and wherein
the disc is provided with two or more steps configured to limit elastic deformation of the coupling portion, the steps having different heights such that different steps define different levels of actuation of the valve assembly and wherein
the coupling portion is provided with a downwards protrusion configured to make contact with the steps of the disc when the coupling portion is deformed such that the different levels of actuation of the valve assembly are defined by rotating the disc such that the protrusion makes contact with a different step when the coupling portion is deformed.

14. The device according to claim 13, wherein the aerosol container contains a therapeutic or prophylactic composition comprising an active ingredient and a pressurized liquid propellant.

15. The device according to claim 14, wherein the aerosol container contains norflurane.

16. The device according to claim 13, and further comprising an extension tube configured to be coupled to the outlet.

* * * * *